United States Patent [19]
Hayes et al.

[11] Patent Number: 6,060,624
[45] Date of Patent: May 9, 2000

[54] RACEMIZATION OF OPTICALLY ACTIVE ALKOXYAMINES

[75] Inventors: Kathryn Sue Hayes, Norristown; Eugene George Lutz, Drums; Michael Gerard Turcotte, Bethleham, all of Pa.

[73] Assignee: Air Products and Chemicals, Inc., Allentown, Pa.

[21] Appl. No.: 09/327,656

[22] Filed: Jun. 8, 1999

[51] Int. Cl.[7] .................................................. C07C 205/00
[52] U.S. Cl. .............................................................. 564/302
[58] Field of Search ............................................... 564/302

[56] References Cited

U.S. PATENT DOCUMENTS

| | | |
|---|---|---|
| 3,954,870 | 5/1976 | Fukumaru et al. . |
| 3,970,700 | 7/1976 | Nagase et al. . |
| 4,096,186 | 6/1978 | Ichikawa et al. . |
| 4,990,666 | 2/1991 | Harsy . |
| 5,847,215 | 12/1998 | Ditrich . |

FOREIGN PATENT DOCUMENTS 2903589  8/1914  Germany .

*Primary Examiner*—Paul J. Killos
*Attorney, Agent, or Firm*—Mary E. Bongiorno

[57] ABSTRACT

A method for racemizing an enantiomer of an alkoxyamine represented by formula I

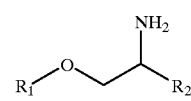

I in which $R_1$ and $R_2$ are the same or different $C_1$ to $C_{20}$ alkyl group. A feed containing an enantiomer of the alkoxyamine is passed over a nickel or cobalt catalyst in the presence of hydrogen and ammonia. The racemic mixture formed by this method contains substantially no by-products.

16 Claims, No Drawings

RACEMIZATION OF OPTICALLY ACTIVE ALKOXYAMINES

BACKGROUND OF THE INVENTION

Alkoxyamines represented by formula I,

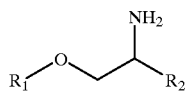

I in which $R_1$ and $R_2$ are, independently, $C_1$ to $C_{20}$ alkyl groups, are important intermediates for compounds used in pharmaceutical and agricultural applications. Due to the presence of an asymmetric carbon atom, the above alkoxyamines exist as a mixture of enantiomers or optical isomers.

It is known that for compounds that exist as optical isomers, one isomer is typically more active than the other, and sometimes one isomer is exclusively active, depending on its use. By using essentially the active enantiomer, lower effective amounts are needed; thus making the production of the active material more cost effective. In addition, if the compound is known to have an adverse effect on the environment, the environmental impact of the enantiomer can be reduced by using lower amounts.

In general, optically active amines are produced in the form of racemic mixtures. Methods which have been used to obtain the active isomer include asymmetric synthesis, resolution of the enantiomers in racemic mixtures, and selective reaction. When the enantiomers are separated by techniques such as selective reaction or resolution, the inactive enantiomer is recovered along with the active enantiomer. If an outlet cannot be identified for the inactive isomer, it becomes a waste stream. A goal in the industry is to maximize production of the active isomer and minimize the environmental impact of an inactive isomeric waste stream. Therefore methods of limiting the amount of inactive isomer produced is of continuing interest. One method of limiting the amount of inactive isomer has been to convert the inactive isomer to the racemic mixture and then recycle the racemic mixture to a separation process. However, one of the problems encountered in producing racemic mixtures is the production of undesirable by-products.

The following patents provide examples of methods which have been used to produce racemic mixtures of optically active amines.

U.S. Pat. No. 3,954,870 (Fukumaru et al., 1976) discloses racemization of optically active α, β-diphenylethylamine by heating the optically active amine at a temperature between 100° C. and the b.p. of the amine in the presence of Raney nickel under an inert gas such as nitrogen, helium or ammonia. Hydrogen is not desired because it promotes reduction of the amines and the formation of by-products. It is reported that by using a dry Raney nickel, a short reaction time is realized and the formation of undesired by-products is prevented.

U.S. Pat. No. 3,970,700 (Nagase et al., 1976) discloses a method for racemizing optically active amines by contacting optically active amines of the formula below with an alkali metal deposited on a solid carrier, an alkali metal dispersed in a liquid medium or an alkali metal alloy at a temperature of from −10 to 50° C.:

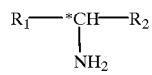

wherein *C is an asymmetric carbon atom, $R_1$ is alkyl, aralkyl or aryl and $R_2$ is aryl or alkoxycarbonyl, the aryl or aralkyl moiety bearing optionally one or more alkyl or alkoxy groups on the aromatic ring, and $R_1$ and $R_2$ are different from each other.

U.S. Pat. No. 4,096,186 (Ichikawa et al., 1978) discloses racemization of optically active aminoalcohol compounds having the following formula:

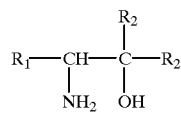

wherein $R_1$ is an alkyl, cycloalkyl, substituted or unsubstituted phenyl, or non-aromatic heterocyclic group, and $R_2$ is a hydrogen atom or an alkyl or substituted or unsubstituted phenyl group. The compounds are contacted with ammonia and hydrogen in the presence of a hydrogenation catalyst such as nickel, cobalt, copper and noble metals; cobalt is preferred, especially cobalt alone or with a small amount of a metal or metal oxide, such as iron, manganese, zinc, and cesium, or the corresponding oxides.

DE 2,903,589 (Vitt, 1980) (abstracts from Derwent World Patent Index and Chemical Abstracts) discloses racemization of amines having the general formula: R1—CH(NH₂)—R2 (where R1 and R2 are different alkyl or aralkyl residues, the aralkyl residue optionally substituted in the aromatic ring with one or more alkyl, fluorinated alkyl, alkoxy or OH). The amines are treated with hydrogen in the presence of a hydrogenation catalyst (preferably Raney cobalt or Raney nickel) at temperatures of 80 to 300° C.

U.S. Pat. No. 4,990,666 (Harsy, 1991) discloses racemization of optically active amino alcohols by subjecting the amino alcohols to hydrogen under moderate temperatures (100 to 175° C.) and pressures (10 to 50 atmospheres) while in contact with Raney cobalt. Ammonia is not required. The process can be batch or continuous. The amino alcohols have the following general formulas:

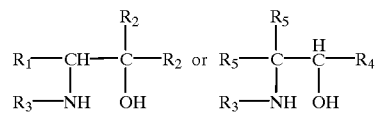

wherein $R_1$ is an alkyl group or cycloalkyl group; each $R_2$ is the same group selected from hydrogen, alkyl group, or cycloalkyl; $R_3$ is a hydrogen atom or an alkyl group; $R_4$ is the same groups as $R_1$; and each $R_5$ is the same group selected from those equal to $R_2$.

U.S. Pat. No. 5,847,215 (Ditrich, 1998) discloses racemization of optically active arylalkylamines by reaction of the amine with a ketone followed by treatment of the condensation product with a base such as an alcoholate or an amine.

BRIEF SUMMARY OF THE INVENTION

The present invention is directed to a process for racemizing an enantiomer of an alkoxyamine having the formula I,

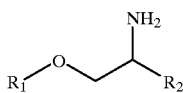

in which $R_1$ and $R_2$ are the same or different $C_1$ to $C_{20}$ alkyl groups.

In this process, an enantiomer of formula I is passed over a nickel or cobalt catalyst in the presence of hydrogen and ammonia to produce a racemic mixture of alkoxyamines containing substantially no by-products. The racemic mixture is useful for isolating one of the enantiomers. Upon removal of the desired enantiomer, the remaining enantiomer can be recycled to the racemization reaction.

This process provides economical and environmental advantages by enabling reuse of the inactive alkoxyamine enantiomer to produce a racemic mixture in high selectivity which contains substantially no by-products.

DETAILED DESCRIPTION OF THE INVENTION

The present invention is directed to a process of racemizing an alkoxyamine enantiomer having the general formula I:

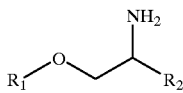

in which $R_1$ and $R_2$ are the same or different $C_1$ to $C_{20}$ alkyl groups. Examples of alkyl groups are methyl, ethyl, propyl, isopropyl, n-butyl, tert-butyl, pentyl, hexyl, and cyclohexyl. $R_1$ and $R_2$ are preferably $C_1$ to $C_4$ alkyl groups; and most preferably, methyl groups.

Enantiomers belong to a general class of compounds called stereoisomers and are structurally characterized as mirror images of each other; i.e., they cannot be superimposed on one another. A racemic mixture contains approximately 50% of each enantiomer.

The catalyst of this invention is a nickel or cobalt catalyst preferably carried on a support such as alumina or silica. The catalyst can contain 20 to 65 wt % nickel or cobalt, preferably, 30 to 55 wt %. The cobalt or nickel catalyst can be prepared by various catalyst preparation methods well known in the art. The metal catalyst is in a salt form, typically an oxide, after preparation and is reduced to the metallic form prior to use in the racemization reaction.

Racemization can be performed in the vapor phase or in the liquid phase; however, the vapor phase is preferred.

In the vapor phase reaction, the temperature can range between about 125 to 300° C.; preferably 150 to 250° C. Reaction pressure can range from atmospheric pressure to about 3000 psig (101 to 20,786 kPa); preferably 50 to 1000 psig (446 to 6,996 kPa).

In general, the following process can be used for racemization. A fixed bed reactor is typically used. The catalyst is reduced in hydrogen at elevated temperatures, e.g., 250 to 450° C. Pressure is increased to reaction pressure and temperature reduced to reaction temperature while maintaining hydrogen flow. A flow of ammonia is then initiated. After 1 to 2 hours, the alkoxyamine is introduced. Ammonia to alkoxyamine mole ratios can be 1/1 to 10/1, preferably 3.5/1 to 7/1. Hydrogen to alkoxyamine ratios can be 1/1 to 10/1, preferably 1.5/1 to 4/1. The gas hour space velocities (GHSV) can be 500/hr to 10,000/hr, preferably 570/hr to 3000/hr.

After racemization, the enantiomeric mixture can be separated from ammonia and any by-products by distillation.

The most preferred compound of this invention, methoxyisopropylamine (MOIPA), may be separated into its enantiomers by any of the previously described methods. The recovered enantiomers may be obtained in an anhydrous state or in a mixture with water corresponding to the MOIPA-water azeotropic composition of about 15–20 wt % water. The racemization process of this invention can be used to convert the azeotropic mixture of water and R- or S-MOIPA to the racemic mixture. The racemic mixture can then be recovered by distillation. Alternatively, the azeotropic mixture can be dried using known methods and the dry MOIPA then racemized.

MOIPA can be produced by amination of methoxyisopropanol. Under the process conditions of this invention, racemization of a single MOIPA enantiomer and amination of methoxyisopropanol can proceed simultaneously. Therefore, the process of this invention can be used to produce a racemic mixture of MOIPA from a feed containing the MOIPA azeotrope and methoxyisopropanol reactant.

The invention will be further clarified by a consideration of the following examples, which are intended to be purely exemplary of the invention.

EXAMPLE 1

RACEMIZATION OF S-METHOXYISOPROPYLAMINE (MOIPA)

A ½-inch stainless steel tubular reactor was charged with 10 cc (8.2 g, −12/+18 mesh) of 42% nickel/alumina catalyst (HSC-102B catalyst supplied by Houdry). The catalyst was reduced in hydrogen at 370° C. for 3 hours. After the reduction was completed, the reactor pressure was increased to 250 psig, hydrogen flow was set to the desired rate, and the reactor temperature was reduced to 190° C. Ammonia was pumped over the catalyst at 10 cc/hour for 2 hours before starting the S-methoxyisopropylamine (MOIPA) (assay, 97.2%, 100% enantiomeric excess (e.e.)) feed. The ammonia flow was reduced to 8 cc/hour, the hydrogen flow was set at 45 sccm, and the S-methoxyisopropylamine flow was initiated at 6.6 cc/hour. Samples of reactor effluent were collected and analyzed for assay and for optical purity using capillary gas chromatographic (GC) methods. Results of the GC analyses showed that the MOIPA assay was 95.9% and the ratio of S- to R-MOIPA was 1.0.

EXAMPLE 2

RACEMIZATION OF ANHYDROUS R-MOIPA

A tubular reactor (½ inch stainless steel) was charged with 10 cc (8.2 g, −12/+18 mesh) of 42% Ni/Al$_2$O$_3$ catalyst (HSC-102B supplied by Houdry). The catalyst was reduced in hydrogen at 370° C. for 3 hours. After completion of the reduction, the reactor pressure was increased to 250 psig, the hydrogen flow was set to the desired rate, and the reactor temperature was reduced to 185° C. Ammonia was pumped over the catalyst at 10 cc per hour (cc/h) for 2 hours before starting the R-methoxyisopropylamine (R-MOIPA) (assay, 92.0%, 88.4% e.e.) feed. The ammonia flow was reduced to 10.2 cc/h, the hydrogen flow was set at 56 sccm, and the R-methoxyisopropylamine flow was initiated at 8.4 cc/h. Samples of reactor effluent were collected and analyzed for assay and for optical purity using capillary GC methods. The analytical results showed that the effluent contained 90.0 wt % methoxyisopropylamine which had an R to S ratio of 1.0.

EXAMPLE 3

RACEMIZATION OF ANHYDROUS R-MOIPA

The procedure of Example 2 was followed except that the temperature was increased to 195° C. The analytical results showed that the reactor effluent contained 89.2 wt % MOIPA with an R/S ratio of 1.0.

EXAMPLES 4–6

RACEMIZATION OF R-MOIPA CONTAINING WATER

The procedure of Example 2 was followed except that the starting R-MOIPA contained 19.6 wt % water and 80.1 wt % R-MOIPA (100% e.e.). The flow rates were set as follows: ammonia, 12.5 cc/h; R-MOIPA/water, 9.6 cc/h; and hydrogen, 56 sccm. The racemization was conducted at 175° C., 185° C. and 190° C. The results are shown below:

| Example | Temperature, ° C. | wt % MOIPA | R/S |
| --- | --- | --- | --- |
| 4 | 175 | 78.5 | 1.1 |
| 5 | 185 | 75.1 | 1.0 |
| 6 | 190 | 74.4 | 1.0 |

EXAMPLES 7–9

RACEMIZATION OF R-MOIPA IN THE PRESENCE OF METHOXYISOPROPANOL

The procedure of Example 2 was followed except that the reactor feed was as follows: 11.3 cc/h of ammonia, 8.6 cc/h of a 50:50 (molar) mixture of methoxyiso-propanol (MOIPOH):R-MOIPA, and 56 sccm of hydrogen. The R-MOIPA contained 19.6% water. Reactor temperatures of 175° C., 185° C., and 190° C. were used. Results are shown in the table below:

| Example | Temperature ° C. | MOIPOH wt % | MOIPA wt % | R/S |
| --- | --- | --- | --- | --- |
| 7 | 175 | 32.6 | 47.1 | 1.0 |
| 8 | 185 | 23.3 | 55.4 | 1.0 |
| 9 | 190 | 20.7 | 57.7 | 1.0 |

The results of Examples 1 through 9 show that a highly selective racemic mixture of MOIPA with very little by-products can be produced using the method of this invention.

EXAMPLES 10–12

EFFECT OF AMMONIA ON RACEMIZATION OF MOIPA

Experiments were conducted to determine the effect of ammonia concentration on methoxyisopropylamine selectivity following the general procedure outlined in Example 2. The reaction temperature for these experiments was 190° C. and the reactor pressure was 250 psig. Other reaction conditions and product yields are shown in the table below:

| Example | Ammonia cc/h | R-MOIPA/water[a] cc/h | Hydrogen sccm | Wt % MOIPA | R/S |
| --- | --- | --- | --- | --- | --- |
| 10 | 12.5 | 9.6 | 56 | 67.7 | 1.0 |
| 11 | 6.5 | 17.9 | 108 | 63.2 | 1.0 |
| 12 | 0 | 33.1 | 122 | 45.8 | 1.1 |

[a]71.2 wt % R-MOIPA, 27 wt % H$_2$O

Examples 10–12 show that, in the absence of ammonia, recovery of MOIPA decreases significantly and racemization effectiveness also decreases.

We claim:

1. A method for racemizing an enantiomer of an alkoxyamine represented by formula I

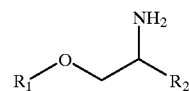

wherein $R_1$ and $R_2$ are the same or different $C_1$ to $C_{20}$ alkyl group, comprising
   contacting a feed comprising said enantiomer with hydrogen and ammonia in the presence of a nickel or cobalt catalyst.

2. The method of claim 1 wherein $R_1$ and $R_2$ are the same or different $C_1$ to $C_4$ alkyl group.

3. The method of claim 1 wherein $R_1$ and $R_2$ are each methyl.

4. The method of claim 3 wherein the catalyst is carried on a support.

5. The method of claim 4 wherein the support is alumina.

6. The method of claim 5 wherein the catalyst contains 20 to 65 wt % nickel or cobalt.

7. The method of claim 5 wherein the catalyst contains 30 to 55 wt % nickel or cobalt.

8. The method of claim 7 wherein the catalyst is nickel.

9. The method of claim 4 wherein the reaction is carried out in the vapor phase at a temperature of 125 to 300° C. and a pressure of 0 to 3000 psig (101 to 20,786 kPa).

10. The method of claim 9 wherein there is an ammonia to alkoxyamine molar ratio of 1/1 to 10/1, a hydrogen to alkoxyamine molar ratio of 1/1 to 10/1, and a gas hour space velocity of 500/hr to 10,000/hr.

11. The process of claim 10 wherein the temperature is 150 to 250° C. and the pressure is 50 to 1000 psig (446 to 6996 kPa).

12. The process of claim 11 wherein the ammonia to alkoxyamine molar ratio ranges from about 3.5/1 to 7/1, the hydrogen to alkoxyamine molar ratio ranges from about 1.5/1 to 4/1, and the gas hour space velocity ranges about 570/hr to 3000/hr.

13. A process for racemizing an enantiomer of methoxyisopropylamine comprising contacting a feed comprising the enantiomer of methoxyisopropylamine with hydrogen and ammonia in the presence of a supported nickel or cobalt catalyst.

14. The process of claim 13 wherein the catalyst is nickel on an alumina support.

15. The process of claim 14 wherein the feed also contains 15 to 20 wt % water.

16. The process of claim 14 wherein the feed also contains methoxyisopropanol.

* * * * *

UNITED STATES PATENT AND TRADEMARK OFFICE
CERTIFICATE OF CORRECTION

PATENT NO. : 6,060,624  
DATED : May 9, 2000  
INVENTOR(S) : Kathryn S. Hayes et al.

It is certified that error appears in the above-identified patent and that said Letters Patent is hereby corrected as shown below:

<u>Column 6,</u>  
Lines 47, 50, 55, 60, 62 and 64, cancel "process" and insert -- method -- therefor.

Signed and Sealed this

Twenty-sixth Day of March, 2002

Attest:

*Attesting Officer*

JAMES E. ROGAN  
*Director of the United States Patent and Trademark Office*